ary Patent [19]

Hobbs

[11] Patent Number: 4,868,206

[45] Date of Patent: Sep. 19, 1989

[54] COMPOSITION FOR RODENT CONTROL

[75] Inventor: David G. Hobbs, Goldsboro, N.C.

[73] Assignee: ICI Americas Inc., Wilmington, Del.

[21] Appl. No.: 933,801

[22] Filed: Dec. 2, 1986

Related U.S. Application Data

[63] Continuation-in-part of Ser. No. 805,834, Dec. 6, 1985, abandoned.

[51] Int. Cl.$^4$ .......................................... A01N 43/18
[52] U.S. Cl. ..................................................... 514/457
[58] Field of Search ........................................ 514/457

[56] References Cited

U.S. PATENT DOCUMENTS

| | | | |
|---|---|---|---|
| 3,764,693 | 10/1973 | Boschetti et al. | 424/281 |
| 3,786,062 | 1/1974 | Schroeder et al. | 260/397.2 |
| 3,843,783 | 10/1974 | Burlow | 424/84 |
| 3,867,546 | 2/1975 | Lechevin | 424/331 |
| 3,929,983 | 12/1975 | Boschetti | 424/17 |
| 3,957,824 | 5/1976 | Hadler et al. | 260/343 |
| 4,021,568 | 5/1977 | Suttle | 424/281 |
| 4,035,505 | 7/1977 | Hadler et al. | 424/281 |
| 4,084,004 | 4/1978 | Dreikorn | 424/330 |
| 4,156,714 | 5/1979 | Lechevin et al. | 424/17 |
| 4,187,318 | 2/1980 | Dreikorn | 424/330 |
| 4,269,820 | 5/1981 | Davies et al. | 425/10 |
| 4,281,471 | 8/1981 | Jenkins et al. | 43/131 |
| 4,304,732 | 12/1981 | McCain, Jr. | 252/549 |
| 4,310,536 | 1/1982 | Boschetti et al. | 424/281 |
| 4,379,139 | 4/1983 | Dawson | 424/84 |
| 4,438,584 | 3/1984 | Baker et al. | 43/58 |
| 4,520,007 | 5/1985 | Entwistle et al. | 424/17 |

FOREIGN PATENT DOCUMENTS

| | | | |
|---|---|---|---|
| 796208 | 9/1973 | Belgium | 514/457 |
| 1371135 | 10/1974 | United Kingdom | 514/457 |

OTHER PUBLICATIONS

Kaukeinen, D. E., "Field Methods for Census Taking of Commensal Rodents in Rodenticide Evaluations", Vertebrate Pest Control and Management Materials, ASTM STP 680, J. R. Beck, Ed., American Society for Testing and Materials, 1979, pp. 68–83.

Morris, K. D. et al., "Design and Evaluation Criteria for Development of Toxic Wicks for Rodent Control", Vertebrate Pest Control and Management Materials: Fourth Symposium, ASTM STP 817, D. E. Kaukeinen, Ed., American Society for Testing and Materials, 1983, pp. 165–182.

Dubock, A. C. et al., "Brodifacoum (TALON TM Rodenticide), A Novel Concept", Eighth Vertebrate Pest Conference, 1978.

Kirk–Othmer, Encyclopedia of Chemical Technology, vol. 18, 3rd Edition, 1982, pp. 308–319.

Primary Examiner—Mary C. Lee
Assistant Examiner—Zinna Northington
Attorney, Agent, or Firm—Denis A. Polyn

[57] ABSTRACT

A composition and a method of using the same wherein said composition comprises a rodenticide and an additive selected from the group consisting of
1. polyoxyalkylated alkyl phenols;
2. sorbitan fatty acids and polyoxyalkylated derivatives thereof;
3. polyoxyalkylated fatty amines;
4. polyoxyalkylated branched or linear alcohols, diols or polyols;
5. polyoxyalkylated branched or linear mercaptans;
6. polyoxyalkylated esters; and
7. polyoxyalkylated amines.

The composition may optionally include an organic solvent and/or a dye. The rodenticide may be selected from a wide host of compounds, including brodifacoum, bromadiolone, diphacinone, chlorodiphacinone, monofluoroacetatic acid, bromethalin, calciferol, flocoumafen, and salts of such compounds.

7 Claims, No Drawings

COMPOSITION FOR RODENT CONTROL

This is a continuation-in-part of copending application Ser. No. 805,834 filed on Dec. 6, 1985, now abandoned.

BACKGROUND OF THE INVENTION

Toxicants applied to the exterior of rodents, referred to as contact toxicants, are of particular importance in those situations where conventional rodent devices, such as baits, are either difficult to apply or are poorly accepted.

Although contact toxicants can be directly applied (e.g. by spraying) to pest animals, the logistics of this approach make passive systems preferable. Passive contact toxicant systems are those wherein the pest animal encounters the toxicant during the course of it's normal movement or behavior. Most passive contact toxicant systems involve tracking powders which are ingested through subsequent grooming activity of the animal after exposure and body contamination. Such formulations, unfortunately, are unable to withstand changes in climatic conditions and therefore contaminate the environment.

Passive contact toxicants are further employed in control devices. An example of such a device is disclosed in U.S. Pat. No. 4,281,471. In this reference, an apparatus characterized by an elongated tube with an interior cross-section is disclosed. Within this interior cross-section is located at least one cartridge onto which is loaded an absorbent material commonly referred to as the "wick." The absorbent material is saturated with a toxic solution. Rodents passing through the elongated tube come into contact with the toxicant formulation. During grooming, the rodent ingests the adhered toxicant and subsequently dies, usually outside the area of contact. This apparatus offers maximum contact between the rodent and pesticide, while substantially reducing chances of contamination to non-target species.

Morris et al, "Design and Evaluation Criteria for Development of Toxic Wicks for Rodent Control", *Special Technical Publication* 817, pp. 165–182, 1984, discusses the feasibility of using similar devices in the control of rodents. In this publication, the toxicant composition applied to the wick is a 0.25% solution of brodifacoum in a propylene glycol solution containing polyethylene glycol of an approximate molecular weight of 200. Unfortunately, rodents often find such toxicant compositions attractive for nesting purposes and thus they readily remove them from the cartridges. Further, this toxic formulation readily absorbs water. Thus, the probability of the formulation leaking off the wick into the interior cross-section of the tube and, thus, into the environment is high. As a result, this composition may contaminate non-target species and the environment. Further, it is unsuitable for use in mass marketing due to it's susceptibility to physical changes in the atmosphere.

SUMMARY OF THE INVENTION

It is an object of this invention to provide a liquid composition for use in rodent control which:
1. contains a lethal dose of rodenticide,
2. is palatable (i.e., non-offensive) to the rodent, but not an attractant such that the rodent removes the wick;
3. is stable (i.e., non-volatile) at high temperatures; and
4. is non-hygroscopic.

It is further an object of this invention to provide a composition for use in rodent control tubular devices, which in addition to the above-identified properties, is also
5. of sufficient viscosity that it adheres to the wick and wicks off onto the rodent without leaking into the tube and/or environment; and
6. is compatible with the plastic material of the elongated tube and/or cartridge.

It is further an object of this invention to provide a rodenticidal composition which is childproof, i.e., not resulting in death upon ingestion.

DETAILED DESCRIPTION OF THE INVENTION

The composition of this invention, particularly useful for the control of rats and mice, has a low vapor pressure. As a result, evaporation of the rodenticide at high temperature is avoided. In addition, the composition does not absorb large quantities of water, especially at low temperatures. Further, since the targeted rodent must ingest, for efficacy purposes, the rodenticidal formulation, the composition preferably should not contain an emetic.

The composition of this invention may be characterized by the following properties:

Vapor Pressure, mm Hg at 25° C., 0.001–20, preferably less than 2.

Viscosity, Brookfield LVT, cps, at 25° C.: 5–800 cps, preferably below 300, most preferably below 250.

Flash Point, Seta-Flash: greater than 100° F.

At room temperature, the composition of this invention is a homogeneous liquid and comprises a rodenticidally effective amount of at least one rodenticide and at least one additive.

The rodenticides of this invention are selected from the group consisting of:
1. 4-Hydroxycoumarin derivatives such as:
A. Compounds of the formula

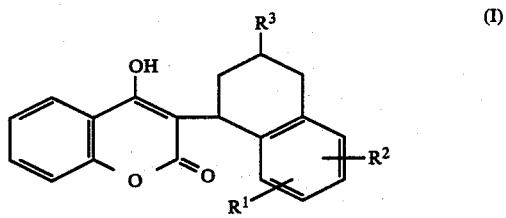

wherein
$R^1$ and $R^2$ are independently selected from the group consisting of hydrogen or halogen atoms (preferably chlorine or bromine) and alkyl or alkoxy groups (preferably having from 1 to 6 carbon atoms),
$R^3$ is an aryl group having the formula

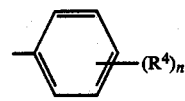

1. where n is 1 or 2, and

R⁴ is independently selected from the group consisting of halogen atoms, a straight or branched chain alkyl or alkoxy group, preferably containing at least 2, more preferably from 5 to 12 carbon atoms, a cycloalkyl, preferably cyclohexyl group, a benzyl, phenyl, halogenophenyl, phenoxy and halogenophenoxy group. The halogen atom or atoms are preferably chlorine or bromine. When n is 1, R⁴ is preferably in the para position and when n is 2, one of the R⁴ groups is preferably in the para position. Preferably R³ contains at least 1 (but not more than 3) and optimally not more than 2 halogen atoms. These compounds are disclosed in U.S. Pat. Nos. 3,957,824 and 4,035,505, which are hereby incorporated by reference.

Especially preferred are the compounds of the structural formulae

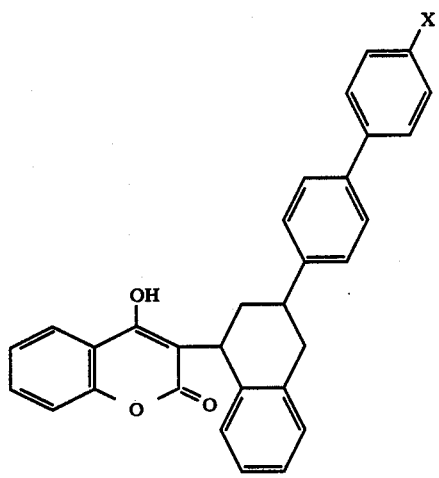

wherein X is hydrogen and bromine, commonly referred to as difenacoum and brodifacoum, respectively;

B. Compounds of the formula

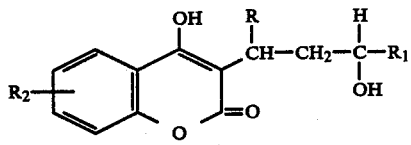

wherein

R is hydrogen, phenyl, halophenyl, dihalophenyl, nitrophenyl, methoxyphenyl, tolyl, methylene dioxyphenyl or furyl, R₁ is methyl, phenyl, halophenyl, nitrophenyl, diphenyl, halodiphenyl, nitrodiphenyl and naphthyl radicals, and R₂ is hydrogen or a halogen.

Such compounds are disclosed in U.S. Pat. No. 3,764,693, herein incorporated by reference. Especially preferred are the compounds wherein R is —H or —C₆H₅; R₁ is —C₆H₅ or —C₆H₄—C₆H₄X wherein X is Br or Cl; and R₂ is H. Especially preferred is the compound wherein R₂ is hydrogen, R is —C₆H₅ and R₁ is

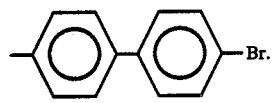

This compound is commonly referred to as Bromadiolone.

C. Compounds of the formula

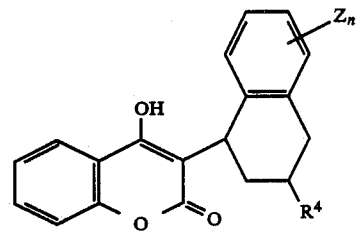

in which Z represents a halogen atom, preferably a chlorine atom, and n is 0, 1 or 2 and R⁴ represents either (1) a grouping which comprises a phenylene radical attached directly or indirectly to the tetralin ring and having in the para position (with respect to such attachment) an electron-withdrawing atom or group whose rotational volume substantially does not exceed that of a phenyl group and which forms together with said phenylene radical a polarisable structure, or (2) a grouping selected from:

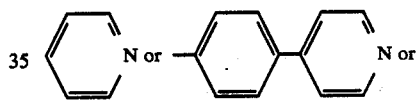

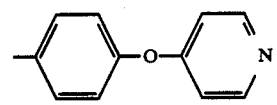

or (3) a grouping which comprises a phenylene radical attached directly to the tetralin ring and having in the para position (with respect to such attachment) a substituted furanyl or thiophenyl radical attached thereto directly or through oxygen and/or methylene, said furanyl or thiophenyl radical having an electron-withdrawing atom or group as a substituent in a position forming with the furanyl or thiophenyl radical a polarisable structure, said atom or group having a rotational volume which substantially does not exceed that of a phenyl group and halogenated derivatives thereof.

Preferred compounds are those in which R⁴ represents a grouping (1) above, which includes a phenylene radical. When such phenylene radical is attached directly, or through another phenylene radical only, or through an oxygen atom and another phenylene radical to the tetralin ring the electron-withdrawing atom or group should not be a halogen atom. Preferably, the just-stated preferred compounds are compounds in which the R⁴ substituent in the tetralin ring contains two-linked phenylene radicals, the outer one being attached to the para position of the inner one (itself attached in the para dash position to the tetralin ring) by a linear or essentially linear radical selected from: —O—(CH₂)m—; —(CH₂)ₘ—O—; —O—(CH₂)ₘ—O—; —(CH₂)ₘ—O—(CH₂)ₚ—; —(CH₂)ₘ—; and the sulphur analogues thereof, in which m is 1 to 6 and p is 1 to 6. When said linking radical is —(CH$_2$)$_m$—, it is noted that such a radical represents the specific selection of a chain of from 1 to 6, preferably 2 to 4, more preferably 3, methylene radicals.

Most preferred are the compounds wherein R$^4$ is one of the following:

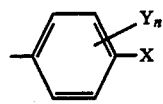 (a)

wherein X is as defined below preferably CN or CF$_3$, and n is 0, 1 or 2, provided that when n is 1 or 2, Y is fluorine or chlorine in a position adjacent to X

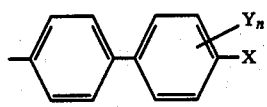 (b)

wherein X is as defined below, preferably CN or CF$_3$ and Y is fluorine or chlorine, and n is either 0, 1 or 2 provided that when n is 1 or 2, Y is in a position adjacent to X and X can also be a halogen atom

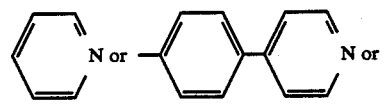 (c)

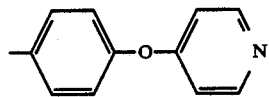

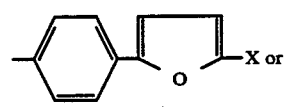 (d)

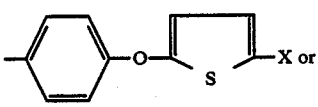

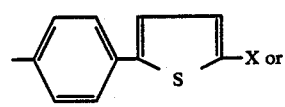

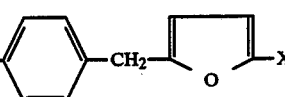

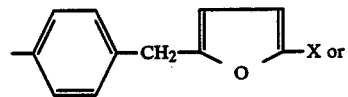

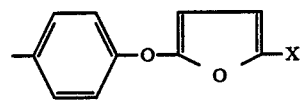

wherein X is as defined below, or is a halogen atom, preferably a bromine atom

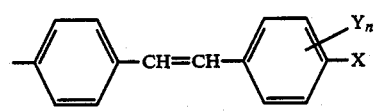 (e)

wherein X is as defined below and n=0, or is a halogen atom and Y is a halogen atom and n is 1 or 2.

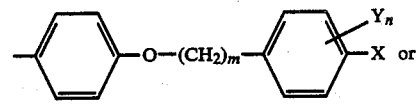 (f)

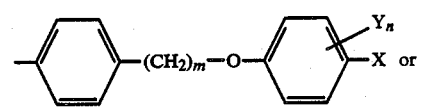 or

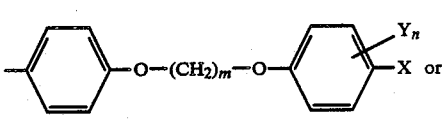 or

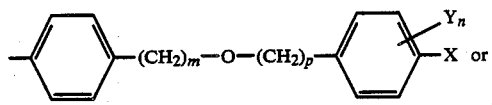 or

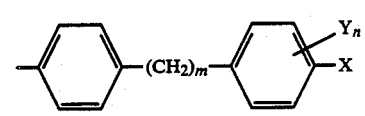

wherein X is as defined below and n=0, or is a halogen atom. Y is a halogen atom and n is 1 or 2, and m is 1 to 6 and p is 1 to 6, together with the sulphur analogues of the above structures in which an S atom replaces one or both O atoms.

In such compounds X is selected from the group consisting of CN; NO$_2$; SO$_2$R$^5$; CF$_3$; OCF$_3$; COOR$^6$; COR$^7$ and

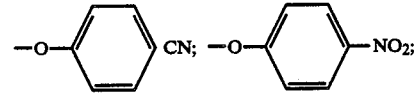

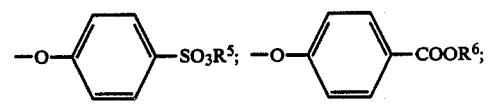

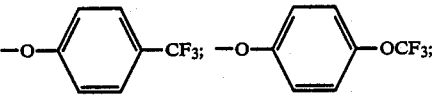

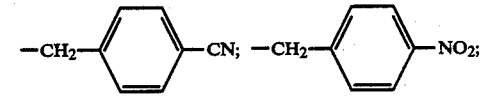

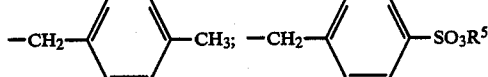

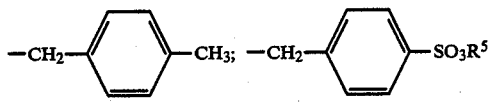

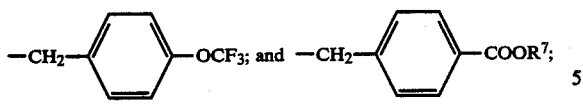

in which $R^5$, $R^6$ and $R^7$ signify alkyl groups especially $C_1$ to $C_4$ alkyl groups. Of these, the —CN and —$CF_3$ groups are particularly preferred. Especially preferred are compounds wherein Z is chlorine, n is 0, 1 or 2 and $R^4$ represents

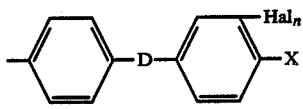

in which Hal is a fluorine or chlorine atom and n is 0 or 1, X is a fluorine, chlorine or bromine atom or a —CN, —$CF_3$ or —$OCF_3$ group and D represents —$OCH_2$— or —$(CH_2)_m$— where m is 2 to 3; and most especially the compound 4-hydroxy-3-(1,2,3,4-tetrahydro-3-[4-(4-trifluoromethylbenzyloxy)phenyl]-1-naphthyl) coumarin represented by the formula

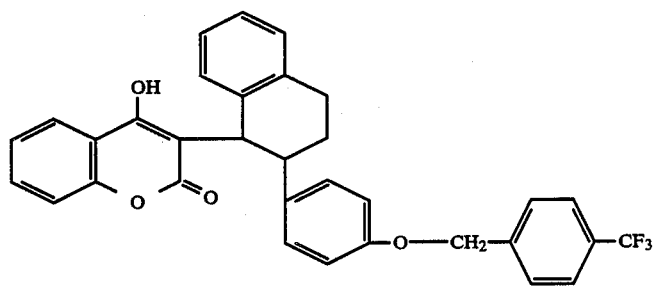

most commonly referred to as Flocoumafen. These compounds are further discussed in U.S. Pat. No. 4,520,007.

2. Indandione derivatives, such as 1,1-diphenyl-2-acetyl-1,3-indandione, commonly referred to as Diphacinone and (1'-parachlorophenyl-1'-phenyl)-2-acetyl-1,3indandione, commonly referred to as Chlorodiphacinone; and 3. Monofluoroacetic acid.

4. Compounds of the formula

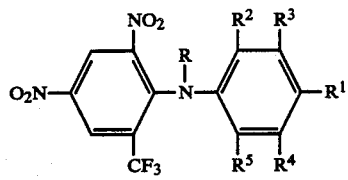

wherein
R represents methyl, ethyl or propyl;
$R^1$ represents hydrogen, fluoro, chloro, bromo, iodo, cyano, methyl, nitro or trifluoromethyl;
$R^2$ and $R^5$ independently represent hydrogen, fluoro, chloro, bromo, nitro, methyl or trifluoromethyl, provided that no more than one of $R^2$ and $R^5$ represents nitro;

$R^3$ and $R^4$ independently represent hydrogen, methyl, fluoro, chloro, bromo or trifluoromethyl; provided that (a) no more than one of $R^1$, $R^2$, $R^3$, $R^4$ and $R^5$ represents methyl, except that $R^3$ and $R^4$ may both represent methyl;

(b) when $R^1$, $R^2$, $R^3$, $R^4$ or $R^5$ represents methyl or fluoro, two or three of $R^1$, $R^2$ or $R^5$ represent chloro or bromo;

(c) no more than one of $R^1$, $R^2$, $R^3$, $R^4$ and $R^5$ represents trifluoromethyl, except that $R^3$ and $R^4$ may both represent trifluoromethyl;

(d) when $R^2$ or $R^5$ represents trifluoromethyl, $R^1$ represents chloro or bromo;

(e) when one and only one of $R^3$ and $R^4$ represents trifluoromethyl, two or three of $R^1$, $R^2$ and $R^5$ represent chloro or bromo;

(f) no more than four of $R^1$, $R^2$, $R^3$, $R^4$ and $R^5$ represent hydrogen;

(g) two fluorine atoms are not adjacent to each other;

(h) when $R^2$ or $R^5$ represents nitro, $R^1$ represents chloro, bromo or nitro;

(i) when $R^1$, $R^2$, $R^3$, $R^4$ and $R^5$ represents trifluoromethyl, none of $R^1$, $R^2$, $R^3$, $R^4$ and $R^5$ represents fluoro or methyl.

These compounds are disclosed in U.S. Pat. No. 4,187,318. Especially preferred is the compound wherein R is —$CH_3$, $R^1$, $R^2$ and $R^5$ are bromine and $R^3$ and $R^4$ are hydrogen, i.e. N-methyl-2,4-dinitro-N-(2,4,6-tribromophenyl)-6-(trifluoromethyl) benzeneamine, more commonly referred to as Bromethalin.

5. Vitamin D compounds, such as calciferol (ergocalciferol) and cholecalciferol. Such compounds are especially preferred when used in combination with any other rodenticide referred to herein.

Further included as compounds in this invention, are the 4-hydroxy coumarin derivatives Dicoumarol, Coumatetraly and Coumachlor and the indanedione derivative Pindone.

Further, salts of the aforementioned compounds may be employed. Such salts are generally formed by the reaction of the selected rodenticide with a salt-forming agent selected from the group consisting of:

(i) an alkali metal, such as sodium or potassium, or the hydroxides thereof;

(ii) ammonia or ammonium hydroxide; and (iii) a conventional amine.

Preferred as the amine are (a) alkanolamines of the formula $N[(C_nH_{2n})_yOH]_x(H)_z$ wherein n=1 to 6, x and y are independently 1 to 3, z is 0 to 2 and further wherein x+z=3. Especially preferred is the alkanolamine wherein n=2, y=1 and x=3; and (b) amines of the formula $$R^1-N(R^2)-R^3-(OR^4)_p OH$$

wherein $R^1$ and $R^2$ are independently hydrogen, methyl, ethyl, propyl or iso-propyl; $R^3$ and $R^4$ are independently $-CH_2-$, $-CH_2CH_2-$, $-CH_2CH_2CH_2-$, and $-CHCH_2-$ with a $CH_3$ branch;

and p is either 0 or 1.

The compounds useful as rodenticides in this invention are more fully discussed in Kirk-Othmer, *Encyclopedia Of Chemical Technology*, Vol. 18, 3rd Edition, pps. 308–318 (1982), which is hereby incorporated by reference along with the references discussed therein. Further, combinations of the above rodenticides may also be employed.

The total amount of rodenticide normally employed in the composition is between 0.05 and 15.0, preferably between 0.15 and 5.0, most preferably 0.25, percent of the total weight of the composition.

Of the above rodenticides, especially preferred are brodifacoum and difenacoum and their metal, ammonium and amine salts since they are more effective at lower concentrations and against rodent populations resistant to such rodenticides as chlorophacinone, diphacinone, and warfarin.

The additives of this invention modify the viscosity and other physical properties of the composition such that water absorption, wick adhesion, palatibility, structural compatibility and rodenticidal effect are optimized. In particular, the additives of this invention must;

(a) absorb less than fifteen percent moisture when exposed to 55% humidity at 5° C. in a 3 inch diameter open petri dish for 72 hours;

(b) undergo less than five percent weight loss when exposed to 55% humidity at 50° C. for 72 hours in a 3 inch diameter open petri dish; and (c) have a viscosity less than 800 centepoise (cps) at 25° C.

Such additives may be selected from the group consisting of 1. polyoxyalkylated alkyl phenols;
2. sorbitan fatty acids and polyoxyalkylated derivatives thereof;
3. polyoxyalkylated fatty amines;
4. polyoxyalkylated branched or linear alcohols, diols or polyols; (This group can also be referred to as polyoxyalkylated ethers.)
5. polyoxyalkylated branched or linear mercaptans;
6. polyoxyalkylated esters; and
7. polyoxyalkylated amines.

The polyoxyalkylated alkyl phenols are produced by condensing 1 mole of a higher alkyl phenol with between 1.0 and 12.5 moles, preferably 6 to 11 moles, of alkylene oxide, preferably ethylene and/or propylene oxide. The phenol typically contains one or more $C_4$ to $C_{12}$ alkyl group(s). Nonyl and octyl phenols are especially preferred. Examples include the condensation products of 1 mole of nonyl phenol and its isomers and 4, 5 and 10 moles of ethylene oxide.

The sorbitan fatty acid is derived from 1 mole of sorbitan and between one and three moles of at least one $C_8$ and $C_{16}$ saturated or unsaturated fatty acid such as lauric, palmitic, myristic and oleic acid. Examples of suitable sorbitan fatty acids include sorbitan monolaurate, sorbitan monopalmitate, sorbitan monostearate, sorbitan monooleate, and sorbitan trioleate.

The polyoxyalkylated sorbitan fatty acid esters are derived from 1 mole of the above described sorbitan fatty acid and between 1.0 and 12.5, most preferably 5, moles of alkylene oxide, preferably ethylene and/or propylene oxide. Specific examples of polyoxyalkylated sorbitan fatty acid esters suitable as additives in this invention include the condensation products of 20 moles of ethylene oxide and 1 mole of either sorbitan monooleate, sorbitan monolaurate or sorbitan tall oil esters.

The polyoxyalkylated fatty amines are produced by reacting 1 mole of a $C_{12}$ to $C_{18}$ saturated or unsaturated fatty amine, most preferably a $C_{15}$ fatty amine, with between 1 and 16 moles of alkylene oxide, preferably ethylene and/or propylene oxide, most preferably ethylene oxide. Suitable fatty amines are oleyl, coco, soya and lauryl amines. Examples of polyoxyalkylated fatty amines include the reaction product of 1 mole of oleylamine and 5 moles of ethylene oxide; and the reaction product of 1 mole of the aminated derivative of tall oil and 16 moles of ethylene oxide.

The polyoxyalkylated branched or linear alcohols, diols or polyols are derived from 1 mole of a $C_{10}$ to $C_{15}$ saturated or unsaturated primary, secondary or tertiary alcohol and between 1 and 15 moles of alkylene oxide, preferably ethylene and/or propylene oxide. Examples of polyoxyalkylated branched linear alcohols include the reaction product of 2 moles of ethylene oxide and 1 mole of olelyl alcohol; 8 moles of ethylene oxide and 1 mole of 2,4,7,9-tetramethyl-5decyn-4,7-diol; a $C_{11}$–$C_{15}$ secondary alcohol with 7 or 9 moles of ethylene oxide; 1 mole of tridecyl alcohol and 6 moles of ethylene oxide; 1 mole of tridecyl alcohol and 8 moles of ethylene oxide; and 1 mole of 2,6,8-trimethylnonanol and 6 moles of ethylene oxide.

The polyoxyalkylated branched or linear mercaptans are the reaction products of (i) one mole of mercaptan of the formula RSH, were R is a $C_7$ to $C_{30}$ saturated alkyl group and (ii) between 1 and 16 moles of alkylene oxide, preferably ethylene and/or propylene oxide. An example of this additive is the reaction product of 1 mole of dodecyl mercaptan and 8 moles of ethylene oxide.

The polyoxyalkylated esters are of the formula $$R-\overset{O}{\underset{\|}{C}}-O(CH_2CH_2O)_x R^1$$

wherein
R is a saturated or unsaturated aliphatic or acyclic $C_{10}$–$C_{22}$ group,
$R^1$ is —H or $$-\overset{O}{\underset{\|}{C}}-R;$$

and
X is between one and eighteen.
These esters are produced by reacting one mole of the appropriate acid with between 1 and 18 moles of alkylene oxide, preferably ethylene and/or propylene oxide.

An example of such an additive is polyoxyethylene (10) glycol oleate.

The polyoxyalkylated amines employed in this invention are selected from the group consisting of

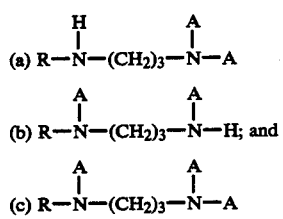

wherein

R is a $C_{12}$ to $C_{18}$ saturated alkyl group;

A is independently $(CH_2CH_2CH_2O)_X$ H or $(CH_2CH_2O)_X$ H wherein X is between 1 and 14 and further wherein the sum of all X's in any one compound is not greater than 15.

Suitable methods for producing the above polyoxyalkylated additives are well known in the art and are discussed in many standard textbooks; such as the Surfactant Science Series, Vol. I to VII, Martin J. Schick, ed., Marcel Dekker, Inc., publisher, and particularly Vol. I, entitled Nonionics.

Further, combinations of the above additives may also be employed. The total amount of such additive in the composition is between 70–90%, preferably 80–90%, most preferably 87%, based on the weight of the total composition.

Further, the composition may also contain an organic solvent. This solvent serves to enhance the shelf life of the liquid concentrate and further, serves to solvate the amine salt in the additive. Generally any organic solvent or combination of organic solvents miscible with the above-identified additives and rodenticides and which permit the composition of this invention to have the following characteristics:

(a) absorbs less than fifteen percent moisture when exposed to 55% humidity at 5° C. in a 3 inch diameter open petri dish for 72 hours;

(b) undergo less than five percent weight loss when exposed to 55% humidity at 50° C. for 72 hours in a 3 inch diameter open petri dish; and (c) have a viscosity less and 800 centepoise (cps) at 25° C.

may be employed. Preferred are polyalkylene polyols, especially those of molecular weight between 100 and 600. Polyethylene glycol and polypropylene glycol are especially preferred. Most preferred is a polyethylene glycol of molecular weight 200. The amount of solvent normally employed in the formulation is between 2 and 50%, preferably between 2 and 10%, based on the total weight of the composition.

Further the composition may contain any conventional dye that is fluoroscent and soluble in the composition. Such dyes have a three-fold purpose.

1. Analytical Tool. The fluoroscent dyes are employed to determine the relative amount of rodenticide in any given sample or the relative amount of rodenticide uptake in a given subject. Further, due to the high level of toxicity of the colorless rodenticides of this invention, appropriate precautionary measures can be undertaken after this quantity is determined.

2. Use in Field Operations. When employed in the above-discussed tubular rodent control devices, the amount of dye present in any given sample may also be used to determine the efficacy of the wick. This can be ascertained by measuring the amount of dye uptake (which is analogous to the uptake of the active ingredient) by the rodent per pass over the wick, as outlined in the Morris et al article cited above.

3. Contamination of Substrate. It is often necessary to determine how much rodenticide is contaminating the substrate. Thus, for example, the amount of rodenticide in wood can be ascertained by extracting the dye from the wood and calculating the corresponding rodenticide content.

Examples of especially suitable dyes are listed in D. M. Marmion, *Handbook of U.S. Colorants for Food, Drugs and Cosmetics*, John Wiley and Sons, 1984, which is herein incorporated by reference. Especially preferred are:

A. fluorescent dyes selected from the group consisting of fluorescein dyes such as fluorescein (D & C Yellow #7) and its metal (e.g. Ca, Na) salts; 4-iodofluorescein; 4,5-diiodofluorescein; and 2,4,5,7-tetraiodofluorescein;

B. Xanthenes such as D & C Yellow #5; Rhodamine B (D & C Red #19); D & C Yellow #10 (quinoline yellow, i.e. the disodium salt of 2-(2-quinolyl)-1,3-indandione); and D & C Yellow #11 (quinoline yellow SS); and C. F D & C Blue #1, Brilliant Blue FCF. Combinations of dyes may also be employed. The total amount of dye normally employed is between 0.01 to 2%, most preferably 0.1 and 0.2% by weight of the total composition.

While the composition of this invention may be produced by processes known in the art, two processes are especially preferred. In the first, the rodenticide and additive and, optionally, solvent, and/or dye are simultaneously mixed and stirred between 20° and 30° C., preferably room temperature, from 30 seconds to 3 days depending on such factors, well known to one skilled in the art, as volume, agitator shear, temperature of the reaction vessel, and product solubility. The mixture is sufficiently blended when the resulting composition remains homogeneous.

If the rodenticide employed is to be a metal, amine or ammonium salt of one of the aforementioned compounds, the appropriate salt-forming agent is also simultaneously mixed with the above components. Alternatively, the metal, ammonia or amine salt may be formed prior to admixing with the rodenticide with the other components of this invention.

The sequential process is especially useful when the rodenticide employed is a metal, amine or ammonium salt of one of the aforementioned compounds. In this process one of the aforementioned compounds, the salt-forming agent and organic solvent are simultaneously added to a reaction vessel and the mixture stirred from 1 to 7 hours. To the resulting mixture containing the formed rodenticidal salt is added the additive and, optionally, the dye. Alternatively the rodenticide, salt-forming agent and additive may be simultaneously added to the reaction vessel and stirred for 1 to 7 hours. The dye and organic solvent, if desired, may be added either to the reaction vessel during or subsequent to the formation of the rodenticidal salt. In either alternative or in any other feasible method, the components of the composition are stirred between 20° to 80° C., preferably 25° C., for 30 seconds to one day until the resulting composition remains homogeneous. This process may also employ the pre-formed rodenticidal salt.

When the rodenticide soluble salt is formed in one of the above defined in situ processes, the amount of salt-forming agent employed is between 3-50%, preferably 3-10%, most preferably 6%, based on the weight of the total composition.

Especially preferred as the composition of this invention is 0.15 to 5.0 weight percent of a compound of the formula

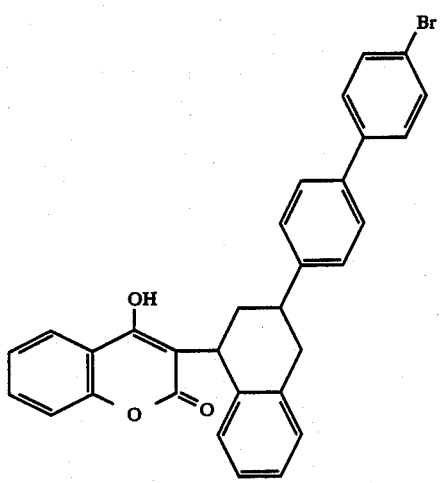

70 to 90 weight percent of the reaction product of an oleylamine and aklylene oxide; 3 to 50 weight percent of triethanolamine; 2 to 10 weight percent of a polyalkylene glycol of molecular weight between 100 and 600; and 0.1 to 0.2 weight percent of Rhodamine B.

While the composition of this invention may be employed in various devices and forms, it is especially adapted for use in a rodent control tubular apparatus. In particular, due to the synergistic effect of the physical properties of the composition, it generally will not leak from the cartridge of such a device when loaded onto the wick and thus the danger of contamination to both non-target species and the environment is eliminated. In such rodent control tubes, the amount of composition added to a single wick is that amount needed to achieve between 50 to 90, most preferably 75-90, percent saturation.

Further, the composition of this invention is considered to be child-proof when employed in such apparatus. The composition is considered to be child-proof since accidental ingestion by a 25 kg child of the composition of this invention from either or both cartridges would not be fatal.

The following non-limiting examples are presented to further illustrate the invention and the advantages thereof.

EXAMPLE 1

To a 250 ml beaker was added 6.12 g of salt-forming agent (triethanolamine) and 6.08 g of solvent (polyethylene glycol 200). A homo-mixer (International Laboratory, Model No. X-1020) was then lowered into the beaker and the mixture was stirred (approximately 30 seconds) until homogeneous. To the resulting blend was added 0.266 g of brodifacoum (technical, 93.89 wt. % active ingredient). After stirring with the homo-mixer for approximately 20 minutes, 0.04 g of Rhodamine B was added to the beaker. The mixture was then stirred for approximately 25 minutes until it was homogenized. 87.494 g of additive (N,N-polyoxyethyl(5)oleylamine) was then added and the composition was stirred until homogenous, approximately five minutes. The resulting composition was characterized as follows:

| | |
|---|---|
| Specific Gravity at 25° C. | 0.9730 |
| Vapor Pressure mm Hg at 25° C.[2] | 2.0 |
| Boiling Point, °C. | 42-280 |
| Viscosity (Brookfield LVT, cps), at 25° C., Spindle #2 at 30 rpm | 135 |
| Flash Point (Seta-Flash, °F.)[2] | >230° |
| % Evaporation at 50° C., 72 hrs., 52% relative humidity (R.H.) (wt. %) | 1.0 |
| % Water Absorption at 5° C., 72 hrs., 52% R.H. (wt. %) | 8.0 |

[2]Brodifacoum not present in composition when this index was obtained.

EXAMPLES 2-9

The procedure of Example 1 was repeated. The reactants employed and their respective amounts are the same as recited in Example 1 except for the additive component. The properties of the resulting formulations are summarized in Table I.

TABLE I

| | Example No. | | | | | | | |
|---|---|---|---|---|---|---|---|---|
| | 2 | 3 | 4 | 5 | 6 | 7 | 8 | 9 |
| Additive (87.49 g) | 1 | 2 | 3 | 4 | 5 | 6 | 7 | 8 |
| Viscosity (cps) Brookfield LVT Spindle #2 at 30 rpm, 25° C. | 155 | 385 | 560 | 120 | 775 | 120 | 85 | 131 |
| % Evaporation at 50° C., 72 hrs., 52% R.H. (wt. %) | 1.5 | 1.0 | 2.5 | 2.0 | 1.0 | 3.0 | 8.5 | 1.2 |
| % Water Absorption at 5° C., 72 hrs., 52% | 9.0 | 2.0 | 10.0 | 11.5 | 3.5 | 9.0 | 4.0 | 6.3 |

TABLE I-continued

| | Example No. | | | | | | |
|---|---|---|---|---|---|---|---|
| | 2 | 3 | 4 | 5 | 6 | 7 | 8 | 9 |

R.H. (wt. %)

1 Polyoxyethylene (3.5) 2,4,7,9-tetramethyl-5-decyn-4,7-diol;
2 Sorbitan trioleate;
3 Polyoxyethylene (20)sorbitan monooleate
4 Polyethylene glycol (10)oleate (the reaction product of 1 mole of oleic acid and 10 moles of ethylene oxide;
5 N,N',N''—tris(2-hydroxyethyl)-N—tallow-1,3-propanediamine;
6 Reaction product of 1 mole of Dodecyl mercaptan and 8 moles ethylene oxide;
7 A branched alcohol ethoxylate comprising the reaction product of 1 mole of 2,6,8-trimethylnonanol and 6 moles of ethylene oxide;
8 Reaction Product of 1 mole of tridecyl alcohol and 8 moles of ethylene oxide.

EXAMPLE 10

To a 250 ml beaker was added 6.06 g of triethanolamine and 6.03 g of polyethylene glycol 200. A homo-mixer (International Laboratory, Model No. X-1020) was then lowered into the beaker and the mixture was stirred until homogeneous, approximately 30 seconds. To the resulting blend was added 0.266 g of brodifacoum (technical, 93.89 wt. % active ingredient) and 20.55 g of polyethylene glycol 400. After stirring with the homo-mixer for approximately 20 minutes, 0.04 g of Rhodamine B was added to the beaker. The mixture was stirred until homogeneous (approximately 25 minutes). 67.054 g of polyoxyethylene (10) nonyl phenyl was added to the composition which was then stirred until homogeneous, approximately 5 minutes. The resulting composition was characterized as follows:

EXAMPLE 11

5 male and 5 female wild house mice (*Mus musculus*) were dusted with an insecticide to control any ectoparasites. Mice were then placed into group enclosures and were given laboratory chow and water ad lib. All mice were held sexes separate for a minimum of 3 weeks to prevent the use of pregnant females as well as to acclimate them to captive conditions. The animals were then weighed and toe-clipped for future identification prior to introduction into the test enclosure. This enclosure was a plastic laundry tub (U.S. Plastics Corp. Model No. 143675) which was 22.9×15.24×7.0 cm. The floor was covered with Bed-O-Cobs animal bedding (The Andersons, Maumee, Ohio) and two nesting boxes (22.9×15.24×7.0 cm) were placed into the enclosure for the mice to nest in. A single food bowl containing Ground Purina laboratory chow (ad libitum) was placed on top of one of the nesting boxes and a second bowl was filled with water and placed on top of the other box. All the animals were conditioned to the actual test environment for 3 days prior to the start of the test period with food consumption being monitored daily. Following the conditioning period, a mouse tube similar to that disclosed in U.S. Pat. No. 4,281,471 was placed along one wall of the enclosure. Each cartridge was loaded with 1.25 g of the composition of Example 1. Two Actimeter motion detection devices were fitted into the tube at a point just in front of the wick so that mouse activity within the tube could be monitored. Actimeters, as described by Kaukeinen in "Field Methods for Census Taking of Commercial Rodents in Rodenticide Evaluations," Vertebrate Pest Control and Management Materials: Second Symposium, ASTM STP 680, American Society for Testing and Materials, Philadelphia, 1979, pp. 68–83 are infrared sensing devices which measure the combination of heat and body movement. These units have an internal memory and can register up to 9999 counts (activations). Counts are a relative index of activity and do not relate to the total number of passages, i.e., Actimeters count activity at a certain point rather than necessarily revealing complete passes through the device. Each of the Actimeters was monitored daily and counts were taken. Food consumption was also monitored daily. Following the third day of the test, all nesting boxes were searched for dead mice. At death or the end of the 15 day treatment period, all mice were reweighed. The results tabulated in Tables I & II below indicates that the composition of Example 1 has good removal qualities such that sufficient toxicant was removed by the rodents in a relatively short period to cause mortality. In this trial, 100% of the mice died with an average day of death at 7.1 days.

TABLE 1

| Animal No. | Sex | Initial Weight | Final Weight | Day of Death |
|---|---|---|---|---|
| 1 | F | 16.5 | 15.5 | 6 |
| 2 | F | 12.0 | 19.1 | 6 |
| 3 | F | 20.5 | 13.9 | 7 |
| 4 | F | 17.3 | 12.2 | 10 |
| 5 | F | 17.1 | 12.3 | 6 |
| 6 | M | 14.6 | 16.0 | 7 |
| 7 | M | 17.5 | 13.7 | 8 |
| 8 | M | 20.3 | 18.3 | 7 |
| 9 | M | 15.0 | 13.7 | 6 |
| 10 | M | 20.9 | 16.7 | 8 |
| AVERAGE | | 17.2 | 15.1 | 7.1 |

TABLE 2

| | CONDITIONING | | | DAY TEST | | | | | | | | | | | | | | |
|---|---|---|---|---|---|---|---|---|---|---|---|---|---|---|---|---|---|---|
| CONSUMPTION | −3 | −2 | −1 | 1 | 2 | 3 | 4 | 5 | 6 | 7 | 8 | 9 | 10 | 11 | 12 | 13 | 14 | 15 |
| (g) | 22.4 | 23.2 | 12.8 | 26.4 | 27.1 | 12.6 | 2.8 | 12.8 | 6.9 | 23.0 | 0.6 | 0.0 | 0.3 | | | | | |
| ACTIMETER COUNTS LEFT | | | | 422 | 196 | 165 | 128 | 96 | 45 | 335 | 8 | 0 | 0 | | | | | |
| ACTIMETER COUNTS RIGHT | | | | 465 | 238 | 161 | 123 | 89 | 69 | 339 | 2 | 0 | 0 | | | | | |

EXAMPLE 12-13

5 male and 5 female wild house mice (*Mus musculus*) were dusted with an insecticide to control any ectoparasites. Mice were then placed into group enclosures and were given laboratory chow and water ad lib. All mice were held sexes separate for a minimum of 3 weeks to prevent the use of pregnant females as well as to acclimate them to captive conditions. The animals were then weighed and toe-clipped for future identification prior to introduction into the test enclosure. This enclosure was a plastic laundry tub (U.S. Plastics Corp. Model No. 143675) which was 22.9×15.24×7.0 cm. The floor was covered with Bed-O-Cobs animal bedding (The Andersons, Maumee, Ohio) and two nesting boxes (22.9×15.24×7.0 cm) were placed into the enclosure for the mice to nest in. A single food bowl containing Ground Purina laboratory chow (ad libitum) was placed on top of one of the nesting boxes and a second bowl was filled with water and placed on top of the other box. All the animals were conditioned to the actual test environment for 3 days prior to the start of the test period with food consumption being monitored daily. Following the conditioning period, a mouse tube similar to that disclosed in U.S. Pat. No. 4,281,471 was placed along one wall of the enclosure. The cartridge was loaded with 1.25 g of the formulation. To the top of the cartridge was placed a 20 mesh screen with 0.02 diameter. The tubes were removed after the fourth day of the test. At death or at the end of the thirteenth day, a body count was made. The results are tabulated in Table II.

TABLE II

| Formulation Employed | % Mortality Male | % Mortality Female | Range of Death (Days) | Average Day of Death |
|---|---|---|---|---|
| Ex. 9 | 60 | 80 | 7–11 | 9 |
| Ex. 10 | 100 | 80 | 6–13 | 8 |

EXAMPLE 14

5 Male and 5 female wild house mice (*Mus musculus*) were placed in separate cages for a period of five days. A food bowl containing Ground Purina laboratory chow and a water bowl was placed in each cage. Each mouse was permitted to pass through a mouse tube similar to that disclosed in U.S. Pat. No. 4,281,471 five times per day. The cartridge of the tube was loaded with 1.25 g of the formulation of Example 10. The mean date of death was 6.8 days±1.6 days. 100% mortality occurred by day 15.

What is claimed is:

1. A homogeneous liquid composition for loading the wick of a rodent control apparatus comprising:
   (I) a rodenticidally effective amount of at least one rodenticide selected from the group consisting of a compound of the formula

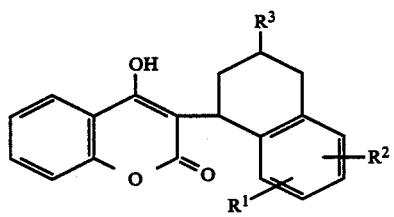

(I)

wherein
   $R^1$ and $R^2$ are independently selected from the group consisting of hydrogen, halogen, a $C_1$–$C_6$ alkyl and a $C_1$–$C_6$ alkoxy group;
   $R^3$ is an aryl group having the formula

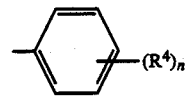

where n is 1 or 2, and
   each $R^4$ is independently selected from the group consisting of halogen, a $C_2$–$C_{12}$ alkyl, a $C_2$–$C_{12}$ alkoxy group, cyclohexyl, benzyl, phenyl, halogenophenyl, phenoxy and halogenophenoxy provided that $R^3$ contains not more than 3 halogen atoms;
and
   (II) between 70 and 90 weight percent of at least one additive which will
   (a) absorb less than fifteen percent moisture when exposed to 55% humidity at 5° C. in a 3 inch diameter open petri dish for 72 hours;
   (b) undergo less than five percent weight loss when exposed to 55% humidity at 50° C. for 72 hours in a 3 inch diameter open petri dish;
   (c) have a viscosity less than 800 centepoise (cps) at 25° C.; and is selected from the group consisting of a
   polyoxyalkylated fatty amine comprising the reaction product of 1 mole of a $C_{12}$ to $C_{18}$ fatty amine and between 1 and 16 moles of alkylene oxide.

2. The composition of claim 1 wherein said composition has a vapor pressure between 0.001–20 mm Hg at 25° C.; a viscosity (Brookfield LVT cps at 25° C.) between 5–800; and a flash point (seta-flash) greater than 100° F.

3. The composition of claim 1 wherein the rodenticide of (I) is of the formula

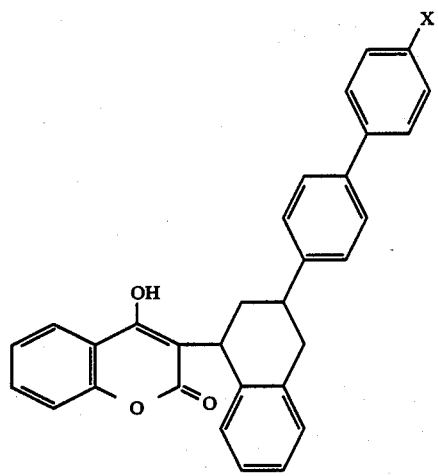

wherein X is either hydrogen or bromine.

4. The composition of claim 1 wherein said $C_{12}$ to $C_{18}$ fatty amine is oleylamine.

5. The composition of claim 1 which comprises 0.15 to 5.0 weight percent of a compound of the formula

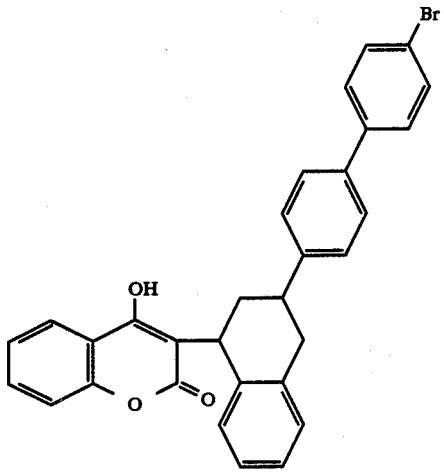

70 to 90 weight percent of the reaction product of an oleylamine and alkylene oxide; 3 to 50 weight percent of triethanolamine; 2 to 10 weight percent of a polyaklylene glycol of molecular weight between 100 and 600; and 0.1 to 0.2 wt. percent of Rhodamine B.

6. A method of killing rodents which comprises loading the wick of a rodent control apparatus with a toxic liquid composition and placing the loaded apparatus in a pathway frequented by rodents, whereby subsequent to the rodent passing through the apparatus and ingesting the composition during grooming the rodent dies, wherein the composition comprises:

(I) a rodenticidally effective amount of at least one rodenticide selected from the group consisting of a compound of the formula

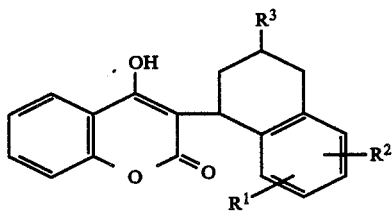

(I)

wherein $R^1$ and $R^2$ are independently selected from the group consisting of hydrogen, halogen, a $C_1$-$C_6$ alkyl and a $C_1$-$C_6$ alkoxy group;

$R^3$ is an aryl group having the formula

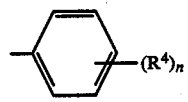

where n is 1 or 2, and each $R^4$ is independently selected from the group consisting of halogen, a $C_2$-$C_{12}$ alkyl, a $C_2$-$C_{12}$ alkoxy group, cyclohexyl, benzyl, phenyl, halogenophenyl, phenoxy and halogenophenoxy provided that $R^3$ contains not more than 3 halogen atoms; and (II) between 70 and 90% weight percent of at least one additive selected from the group consisting of a polyoxyalkylated fatty amine comprising the reaction product of 1 mole of a $C_{12}$ to $C_{18}$ fatty amine and between 1 and 16 moles of alkylene oxide.

7. The method of claim 6 wherein the rodenticide of (I) is of the formula

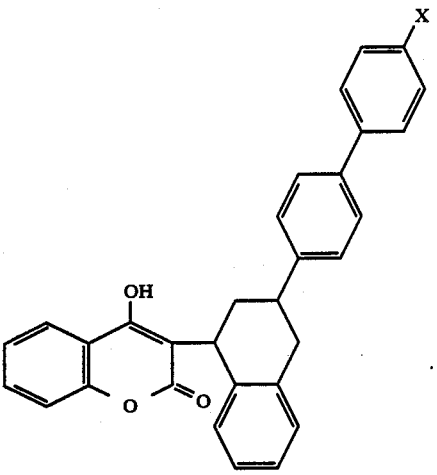

wherein X is either hydrogen or bromine.

* * * * *